(12) United States Patent
Pond et al.

(10) Patent No.: US 10,213,272 B2
(45) Date of Patent: Feb. 26, 2019

(54) PIEZOELECTRIC DEVICE AND CIRCUITRY

(71) Applicant: INTER-MED, INC., Racine, WI (US)

(72) Inventors: Gary J. Pond, Milwaukee, WI (US);
John Baeten, Oak Creek, WI (US);
Michael W. Allen, Shortsville, NY (US)

(73) Assignee: INTER-MED, INC., Racine, WI (US)

( * ) Notice: Subject to any disclaimer, the term of this patent is extended or adjusted under 35 U.S.C. 154(b) by 97 days.

(21) Appl. No.: 15/108,033

(22) PCT Filed: Dec. 29, 2014

(86) PCT No.: PCT/US2014/072589
§ 371 (c)(1),
(2) Date: Jun. 24, 2016

(87) PCT Pub. No.: WO2015/100457
PCT Pub. Date: Jul. 2, 2015

(65) Prior Publication Data
US 2016/0324596 A1 Nov. 10, 2016

Related U.S. Application Data

(60) Provisional application No. 61/986,563, filed on Apr. 30, 2014, provisional application No. 61/921,294, filed on Dec. 27, 2013.

(51) Int. Cl.
*A61C 1/07* (2006.01)
*A61C 17/02* (2006.01)
(Continued)

(52) U.S. Cl.
CPC .............. *A61C 1/07* (2013.01); *A61C 1/0015* (2013.01); *A61C 17/0202* (2013.01); *A61N 7/00* (2013.01);
(Continued)

(58) Field of Classification Search
CPC ..... A61C 1/07; A61C 1/0015; A61C 17/0202; A61C 5/40; A61C 5/50; A61N 7/00; B06B 1/0207; H01L 41/042; H01L 41/09
See application file for complete search history.

(56) References Cited

U.S. PATENT DOCUMENTS 3,975,650 A * 8/1976 Payne .................. B06B 1/0276
310/316.01
4,353,693 A * 10/1982 Dery ...................... A61C 19/04
433/224

(Continued)

FOREIGN PATENT DOCUMENTS

EP             1529570 A2     5/2005

*Primary Examiner* — Cris L Rodriguez
*Assistant Examiner* — Hao D Mai
(74) *Attorney, Agent, or Firm* — Quarles & Brady LLP

(57) ABSTRACT

The present disclosure provides a device having a circuit. The circuit includes at least one boost converter receiving power from an energy source, a square wave driver in series with the boost converter, an inductor in series with the square wave driver for converting a square wave to a sinusoidal wave, and a piezoelectric transducer in series with the inductor, the piezoelectric transducer connectable to a load. The device further includes a phase-locked loop coupled to the circuit to determine a resonance frequency of the piezoelectric transducer when the piezoelectric transducer is connected to the load.

30 Claims, 13 Drawing Sheets

(51) Int. Cl.
  *A61N 7/00*   (2006.01)
  *H01L 41/04*  (2006.01)
  *H01L 41/09*  (2006.01)
  *B06B 1/02*   (2006.01)
  *A61C 1/00*   (2006.01)
  *A61C 5/40*   (2017.01)
  *A61C 5/50*   (2017.01)

(52) U.S. Cl.
  CPC .......... *B06B 1/0207* (2013.01); *H01L 41/042* (2013.01); *H01L 41/09* (2013.01); *A61C 5/40* (2017.02); *A61C 5/50* (2017.02)

(56) References Cited

U.S. PATENT DOCUMENTS

| | | |
|---|---|---|
| 6,157,821 A | 12/2000 | Boesch |
| 2006/0241524 A1 | 10/2006 | Lee |
| 2007/0046143 A1 | 3/2007 | Blandino |
| 2007/0066978 A1* | 3/2007 | Schafer .............. A61B 5/02007 606/128 |
| 2007/0109064 A1* | 5/2007 | Micko .................. G08B 13/191 331/158 |
| 2010/0019833 A1 | 1/2010 | Zang |
| 2010/0236092 A1 | 9/2010 | Causier |
| 2013/0331875 A1 | 12/2013 | Ross |
| 2014/0128779 A1* | 5/2014 | Gibson ................... A61N 7/00 601/2 |

* cited by examiner

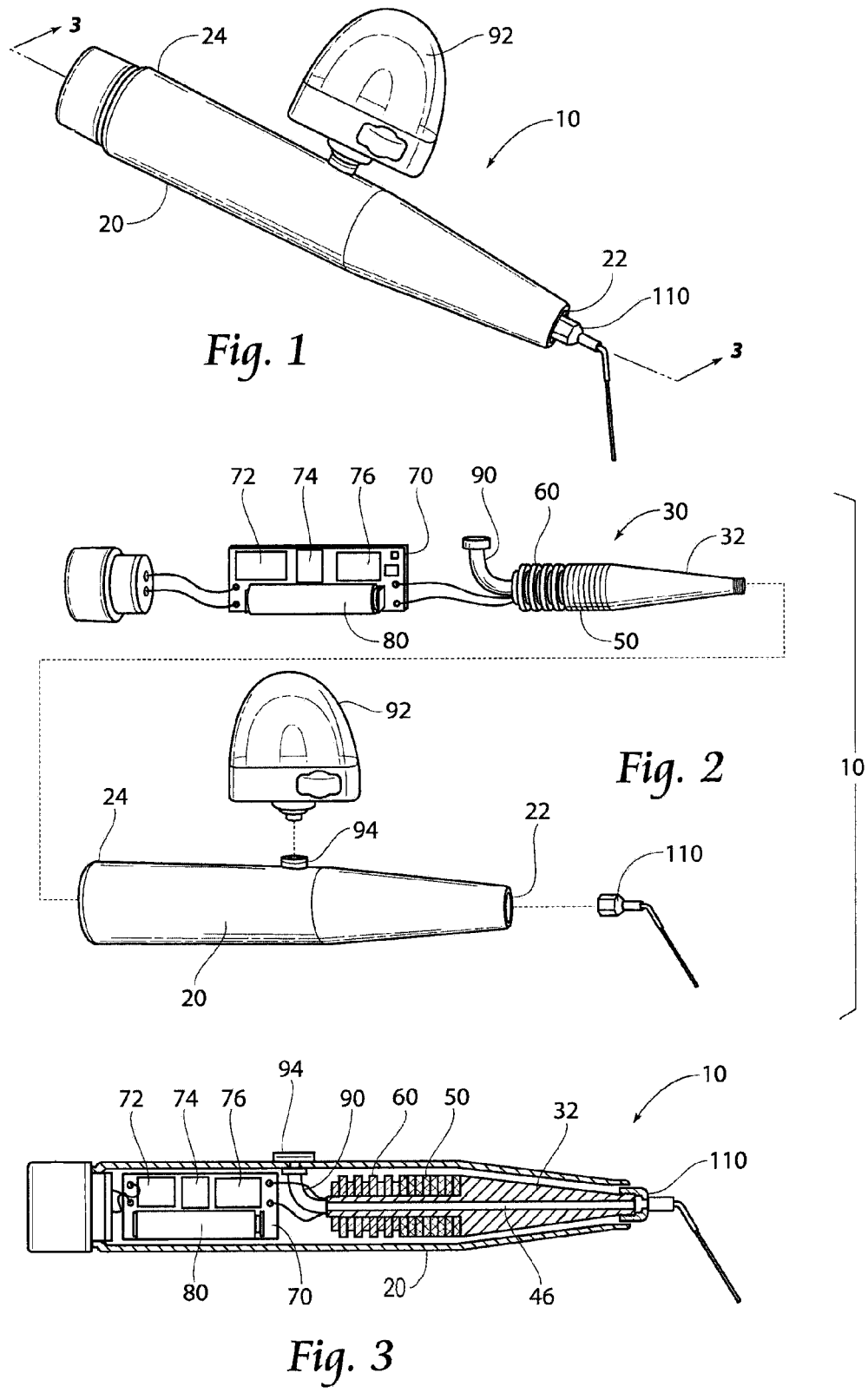

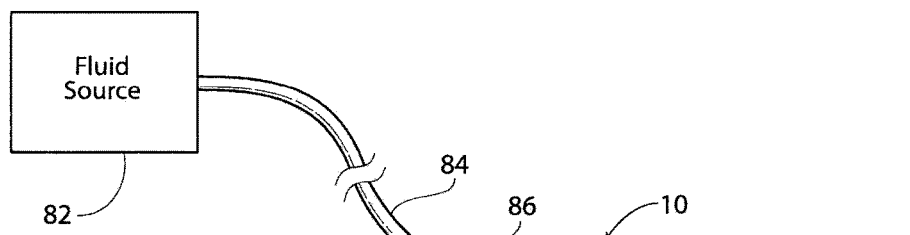
Fig. 10
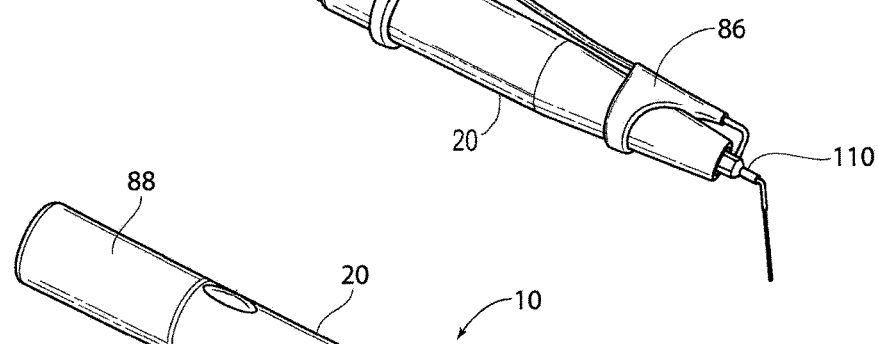
Fig. 11
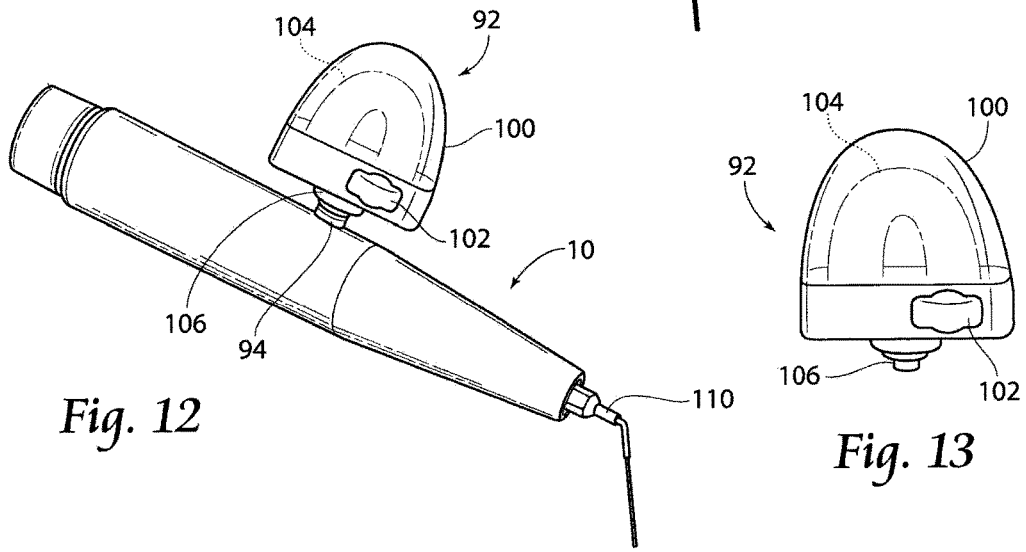
Fig. 12
Fig. 13

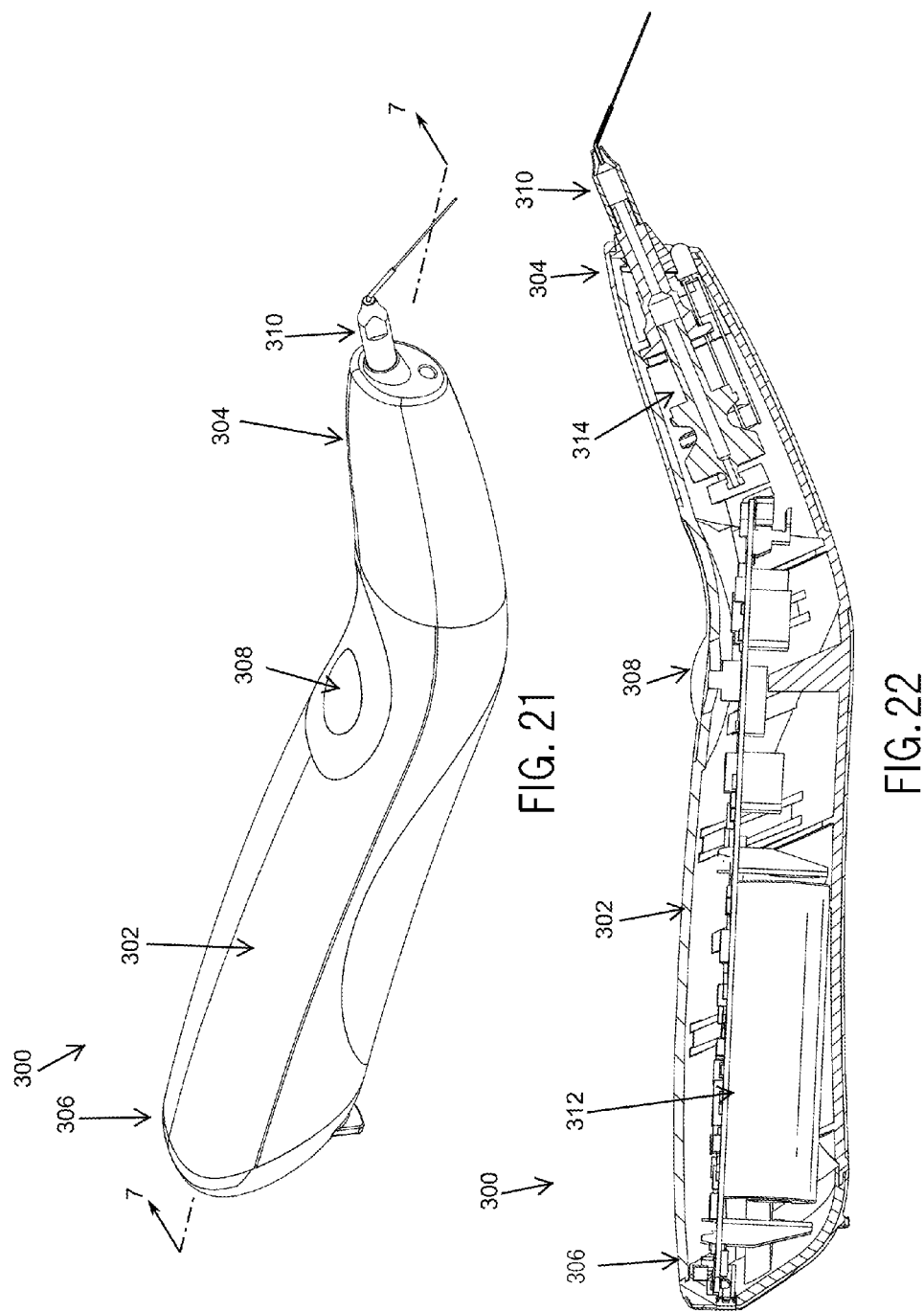

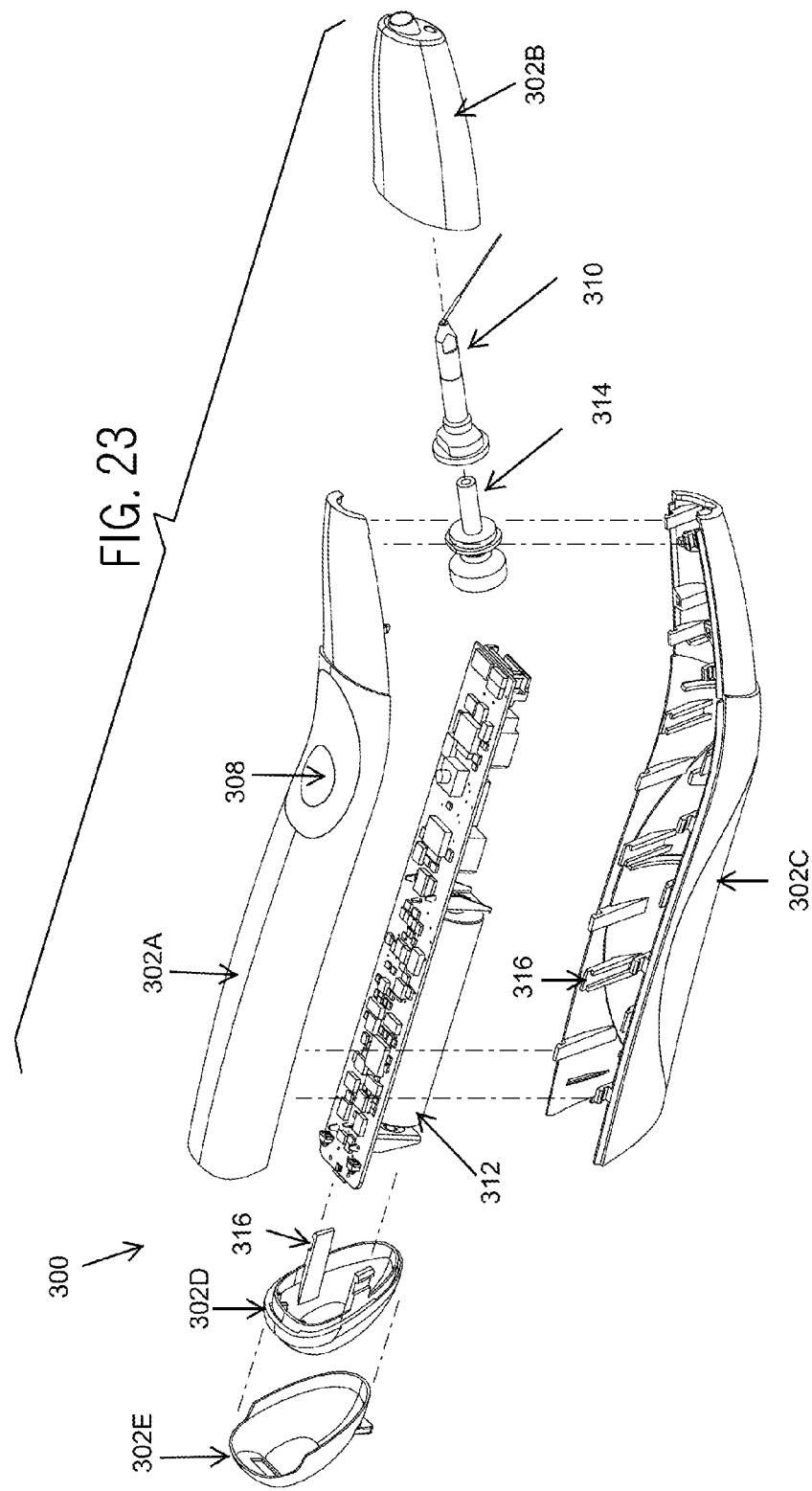

PIEZOELECTRIC DEVICE AND CIRCUITRY

CROSS-REFERENCE TO RELATED APPLICATIONS

This application is related to, claims the benefit of, and incorporates herein by reference U.S. Provisional Patent Application Ser. No. 61/921,294 filed on Dec. 27, 2013 and entitled "Handheld Ultrasonic Instrument," and U.S. Provisional Patent Application Ser. No. 61/986,563 filed on Apr. 30, 2014 and entitled "Handheld Ultrasonic Instrument".

BACKGROUND OF THE INVENTION

The use of powered devices can enhance procedural efficiency and efficacy in the field of dentistry, including endodontic, periodontic, and hygiene procedures. For example, a powered device that provides ultrasonic energy through a treatment tip can result in better cleaning and debridement of hard to reach areas or portions of teeth having a complex geometry in these fields, as well as in oral surgery.

In various situations it can be useful to provide a wired or wireless device for performing a dental or surgical procedure. Devices used in the medical and dental fields such as endodontics, periodontics, hygiene, and other surgical procedures, oral or otherwise, are traditionally performed using hand tools, or externally powered devices. Both are effective, but can have drawbacks. For example, the use of hand tools can result in a lengthier procedure and cause pain, discomfort, or fatigue for the clinician, patient, or both. Powered devices alleviate those problems and can be effective, but can introduce other difficulties. For example, powered devices with cords can be cumbersome to operate because of the fluid connections and cords that add appreciable weight to the device. Further, fluid connections and cords associated with the powered device can be difficult to manipulate during the procedure. During use, care must be taken to avoid tangling of cords, occlusion of fluid pathways, or damage to either.

In the medical field, it can be useful to consider patient safety, time of procedure, and efficacy in the surgical environment when developing new tools and techniques. Like the dental field, powered devices can have advantages over manually powered or unpowered hand tools, including reducing procedure time and providing minimally invasive techniques. However, current powered devices can have drawbacks including insufficient operating life, heavier weight as compared with hand tools, and insufficient available power. Commercially available piezoelectric devices for use in medical and dental procedures can include inefficient drive circuitry that requires higher input power to achieve suitable results. Excess energy is dissipated as heat or other losses, thereby potentially requiring large or higher rated circuit elements, heat sinks and a large device footprint. Previous piezoelectric scaler circuit designs used hard switching and power hungry approaches to force mechanical resonance to occur at a defined electrical signal near the mechanical resonance point. Typically, hard switching was accomplished by connecting a transformer to the piezoceramic which was also connected to "ground." Such electrical circuits are lossy since the energy from each pulse charges the capacitive piezoceramic load and then the energy is discharged to ground. Examples of circuitry employing hard switching for driving ultrasonic devices can be found in U.S. Pat. Nos. 3,596,206, 3,651,352, 4,445,063, and 4,168,447.

In yet another aspect, some prior cordless devices can be coupled to a source of fluid. In order to provide the fluid to the treatment site, a pump, either remote from, or internal to the device, can be used. Internal electronic pumps draw power away from the power supply, which in the case of a battery power supply can drain the battery more quickly.

The control center for existing devices can be located remotely, in which case the operator of the device can need to continually and simultaneously support the device and adjust the control system, which can add time and require additional assistance to complete the procedure. Also, alternating current (AC) powered devices can require features such as shielding from power line voltages and currents.

These and other problems can also arise during operation of an ultrasonic device. Therefore, there is a need for a handheld ultrasonic device that overcomes the aforementioned drawbacks.

SUMMARY OF THE INVENTION

The present disclosure provides a device having a circuit. The circuit includes at least one boost converter receiving power from an energy source, a square wave driver in series with the boost converter, an inductor in series with the square wave driver for converting a square wave to a sinusoidal wave, and a piezoelectric transducer in series with the inductor, the piezoelectric transducer connectable to a load. The device further includes a phase-locked loop coupled to the circuit to determine a resonance frequency of the piezoelectric transducer when the piezoelectric transducer is connected to the load.

In one aspect, the energy source is a direct current rechargeable battery, and is integral to the circuit. In another aspect, the circuit further includes a capacitor in series with the inductor for removing the DC component of the piezoelectric transducer. In yet another aspect, the circuit further includes a capacitor in parallel with the piezoelectric transducer to suppress at least a $3^{rd}$ harmonic mode of vibration of the piezoelectric transducer. In a further aspect, the circuit further includes a pair of back to back diodes in series with the transducer to determine the phase of the current going through the transducer so that it can be fed into the phase comparator of the phase-locked loop.

In one aspect, the circuit further includes a second boost converter in series with the direct current battery. In another aspect, the output of the second boost converter is an input to the phase-locked loop. In a further aspect, the load is a treatment tip for one of a dental and a medical procedure.

In another embodiment, the present disclosure provides a handheld ultrasonic device including a device body having a distal end for coupling to at least one treatment tip, and a circuit within the device body. The circuit includes, at least one boost converter, a square wave driver in series with the boost converter, an inductor in series with the square wave driver for converting a square wave to a sinusoidal wave, and a piezoelectric transducer in series with the inductor. The device further includes a phase-locked loop in a feedback loop. The phase-locked loop is coupled to the circuit to determine a resonance frequency of the piezoelectric transducer when the piezoelectric transducer is connected to the at least one treatment tip.

In one aspect, the circuit further includes an energy source. The at least one boost converter is in series with the energy source. In another aspect, the circuit includes a second boost converter in series with the energy source. In yet another aspect, the output of the second boost converter is an input to the phase-locked loop. In still another aspect, the handheld ultrasonic device further includes a fluid pump. In a further aspect, the fluid pump is one of an elastomeric infusion pump and a piezoelectric pump.

In one aspect, the circuit further includes at least one diode in series with the piezoelectric transducer. In yet another aspect, the handheld ultrasonic device further includes a capacitor in series with the inductor for removing the DC component of the piezoelectric transducer. In a further aspect, the energy source is a rechargeable battery.

These and other aspects and advantages of the device and circuitry disclosed herein will become better understood upon consideration of the detailed description of the drawings.

BRIEF DESCRIPTION OF THE DRAWINGS

FIG. 1 is a perspective view of an embodiment of a handheld ultrasonic device with an attached fluid source according to the present disclosure;

FIG. 2 is an exploded view of the handheld ultrasonic device of FIG. 1;

FIG. 3 is a cross-sectional side view of the device of FIG. 1, taken along line 3-3 of FIG. 1;

FIG. 10 is a perspective view of a dental device according to the present disclosure attached to a remote fluid source;

FIG. 11 is a perspective view of a dental device according to the present disclosure with an attached fluid supply attached to one end of the device;

FIG. 12 is a perspective view of a dental device according to the present disclosure with an attached fluid supply;

FIG. 13 is an elevational side view of the fluid supply of FIG. 10;

FIG. 21 is a perspective view of another embodiment of a device according to the present disclosure;

FIG. 22 is a cross-sectional side view of the device of FIG. 21 as taken along line 7-7 of FIG. 21;

FIG. 23 is an exploded view of the device illustrated in FIG. 21;

DETAILED DESCRIPTION

Figure 4:
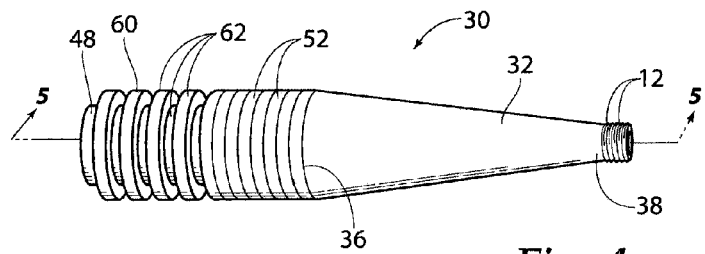
FIG. 4 is a side view of an embodiment of a piezoelectric transducer according to the present disclosure.
Figure 5:
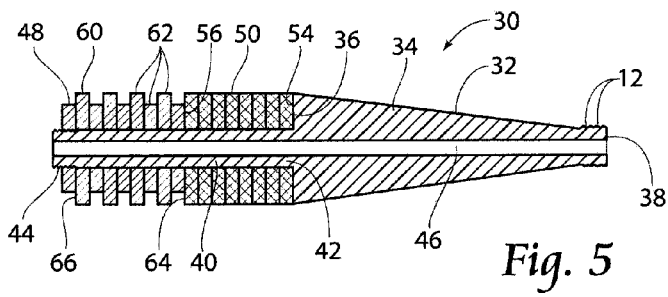
FIG. 5 a cross-sectional side view of the piezoelectric transducer of FIG. 4, taken along the line 5-5 of FIG. 4.
Figure 6:
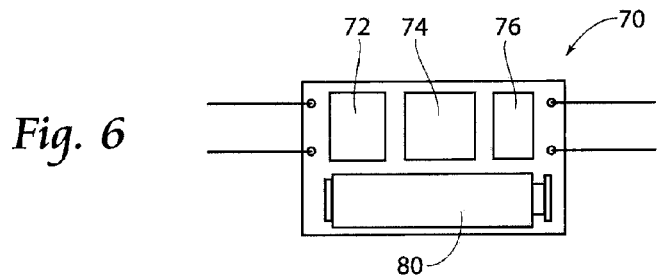
FIG. 6 is an illustration of an embodiment of the internal circuitry of the device of FIG. 1 according to the present disclosure.

Although the disclosure hereof is detailed and exact to enable those skilled in the art to practice the disclosure, the physical embodiments herein disclosed merely exemplify the disclosure which can be embodied in other specific structures. While the preferred embodiment has been described, the details can be changed without departing from the disclosure, which is defined by the claims.

In one aspect, the present disclosure relates to an efficient resonant piezoelectric drive circuit for capacitive loads in piezoelectric ultrasonic devices. The circuit can enhance the overall efficiency and efficacy of such devices, and the efficiency and efficacy of medical or dental procedures that employ such devices, such as an endodontic, periodontal, hygiene, or surgical procedures, including but not limited to bone surgery and soft tissue surgery, or other operations which would benefit from a resonant piezoelectric drive circuit capable of delivering mechanical output at ultrasonic frequencies. The capacitive load can be connected in series to a drive voltage through an inductor and in parallel to a capacitor. Furthermore, the circuit can determine the resonant frequency of a coupled piezoelectric transducer and treatment tip. At resonance, reactive impedances can be reduced or minimized, thereby increasing or maximizing the energy transfer to the treatment tip. However, the resonant frequency can vary depending on the treatment tip. Accordingly, in some embodiments, the circuit can be useful for a handheld ultrasonic device having a piezoelectric transducer for use in a plurality of medical and dental operations. Further, embodiments of the present disclosure can provide for lightweight, compact, cordless, or versatile tools as compared with prior circuit and device designs. The described circuit can have a small physical footprint, require less energy, be powered with a compact rechargeable energy source, or a combination thereof. Circuits and devices according to the present disclosure can be more energy efficient and may dissipate less energy as heat or other losses than other circuits and devices. Moreover, a device according to the disclosure can work with a various known or novel treatment tips. It is contemplated that circuits according to the present disclosure can be useful for inclusion in devices employed for other fields, as will be apparent to one of ordinary skill in the art.

FIG. 1 depicts an embodiment of a handheld ultrasonic device 10 according to the present disclosure that is described in the context of a dental device for use in dental procedures. However, the matter disclosed herein can be utilized in other devices and procedures, as noted. The device 10 generally includes a body 20 having a distal end 22 and a proximal handle end 24. The proximal end 24 can connect to a power source (not shown), that can be a rechargeable energy source such as a supercapacitor, a lithium ion, nickel cadmium or similar battery, a charging station (FIG. 17), or a combination of batteries and a charging station. The distal end 22 can accept various dental tips 110 (also referred to as a treatment tip, surgical tip, dental hygiene tip, or the like), typically via conventional attachment such as threads. Suitable tips include hardened stainless steel geometries that connect to the piezoelectric transducer via threaded connections. Tips for the transmission of ultrasonic energy according to the present disclosure can be formed from materials such as stainless steel, aluminum, copper, brass, nickel, titanium, plastic composites, or a combination thereof. The portion of the tip used for treatment can include various physical characteristics that can influence the cavitation effect of the device such as flutes along the length of the file, tapering from the proximal to distal end of the file, a beveled edge, or the like. Cavitation can be advantageous for various treatments, as cavitation can provide superior cleaning and disinfection as compared with other techniques for cleaning and disinfection. In some embodiments, the present disclosure contemplates the use of treatment tips that can create cavitation within various treatment areas, including root canals, perio pockets or other restricted spaces where displacement of such a tip would be limited or confined.

With reference to FIGS. 1-8, provided at least partially in the body 20 are a power supply 80, a piezoelectric transducer 30, and circuitry 70 that directs and controls power transmission from the power supply 80 to the transducer 30. Nearly all piezoelectric transducers, also called electrostrictive transducers, have the same general construction, and include a piezoelectric stack assembly 50, a back mass 60, and a horn 32. The entire assembly is resonant at a particular operating frequency with the piezoelectric stack assembly 50 being only a small component of the overall assembly. Once assembled, the piezoelectric ultrasonic transducer 30 is resonant over its length. In some cases, this resonance can be essential to proper operation. The transducer 30 is advantageously shaped to minimize its length and width, while maintaining a desirable mechanical resonance frequency when loaded with the dental tip 110 (typically about 25 kHz to about 50 kHz). The total length L of the transducer 30 can be about 40 mm to about 60 mm. However, length L can vary for a particular use or a particular device in which the transducer 30 is placed.

The piezoelectric stack assembly 50 includes at least one piezoelectric disc 52 that can include piezoelectric ceramics or other materials such as lead zirconate titanate, barium titanate, single crystal materials such as quartz, gallium phosphate, and tourmaline, or a combination thereof. In the present example, the piezoelectric discs 52 are encased or sandwiched between two metal back masses 60, and compressed by a bolt or series of bolts through the center of the assembly or around the perimeter of the masses 60 to form a transducer 30 that amplifies the lateral displacement of the piezoelectric discs 52. In some embodiments, the piezoelectric materials are those suited for high-power acoustic applications. The result is the same—compression of the components of the transducer 30. The transducer 30 can have a cymbal transducer design in which the piezoelectric discs 52 are encompassed within two cymbal shaped metal plates that can be used to increase displacement. Alternatively, the transducer 30 can have a Moonie design in which the piezoelectric discs 52 are provided between two metal back masses 60, thereby defining an internal crescent-shaped cavity. These surfaces are on the inner faces of the horn 32 and back mass 60 in direct contact with the piezoelectric ceramic materials.

The piezoelectric stack assembly 50 has a stack first side 54 and a stack second side 56 and includes piezoelectric discs 52. The transducer typically includes at least one piezoelectric disc 52, such as between about 2 and about 8 discs, depending upon the application and the desired operational characteristics. For example, two piezoelectric elements can be arranged to provide additive motion and can be arranged so that their positive faces contact a center electrode insulated from the rest of the assembly. The remaining parts of the assembly including the stack first side and stack second side can be at negative or ground potential and complete the circuit for the negative poles of the piezoelectric elements. This arrangement can ensure that the piezoelectric elements are connected electrically in parallel and mechanically in series.

The back mass 60 helps direct the mechanical vibration output by the piezoelectric stack assembly 50 towards the horn 32. The back mass 60 has a back mass first end 64 and a back mass second end 66. The back mass first end 64 abuts the piezoelectric stack second side 56. Additionally, the back mass 60 can include a solid body having a series of rings 62 of different radii. The different radii allow the back mass 60 to provide the requisite performance characteristics of a similarly performing back mass of a uniform radius and a longer length. Therefore, the back mass 60 decreases the overall weight and length of the device 10. Suitable materials for the back mass 60 include stainless steel, copper, brass, tungsten, titanium, aluminum, and combinations thereof.

The back mass 60 can extend through the piezoelectric stack assembly 50 and horn 32. Additionally (or alternatively), a connector 48 can engage with the horn second segment proximal end 44 and abut the back mass second end 66 to secure the horn 32, the piezoelectric stack 50, and the back mass 60 together.

The horn 32 amplifies mechanical vibrations output by the piezoelectric stack assembly 50. The horn 32 can include titanium, stainless steel, aluminum or another suitable metallic alloy and can have a horn first segment 34 and a horn second segment 40 adjoining the horn first segment 34. The horn first segment 34 has a horn first segment proximal end 36 and a horn first segment distal end 38. The horn first segment proximal end 36 substantially abuts the piezoelectric stack first side 54. The horn first segment 34 is substantially frustoconical and is tapered from the horn first segment proximal end 36 towards the horn first segment distal end 38. The tapered horn first segment 34 promotes amplification of the ultrasonic energy towards the horn first segment distal end 38. The horn first segment distal end 38 can include threads 12, or a quick connect (not shown), that securably connects to and is received by the dental tip 110.

Additional or alternative horn shapes are contemplated wherein a satisfactory amplification of the ultrasonic energy can be achieved. For example, horn designs that would obviate the need for the treatment tip to contain a counterangle are described herein. In one example, a horn shape includes a prebent shaft having a bend between about 50 degrees and about 90 degrees with male threads. Another design includes an angular cut and female threads on the distal end of the horn to allow for tip attachment. Moreover, the horn second segment 40 can include a horn second segment distal end 42, adjoining the horn first segment proximal end 36, and a horn second segment proximal end 44. The horn second segment 40 can be substantially cylindrical.

When a piezoelectric material is properly cut and mounted to create a transducer, it can be made to distort in an electric field (electrostriction or inverse piezoelectricity) by applying a voltage to an electrode near or on the crystal. Upon the application of voltage, the piezoelectric discs 52 experience morphological change, thereby converting electric pulses to mechanical vibration output through the dental tip 110.

Figure 27:
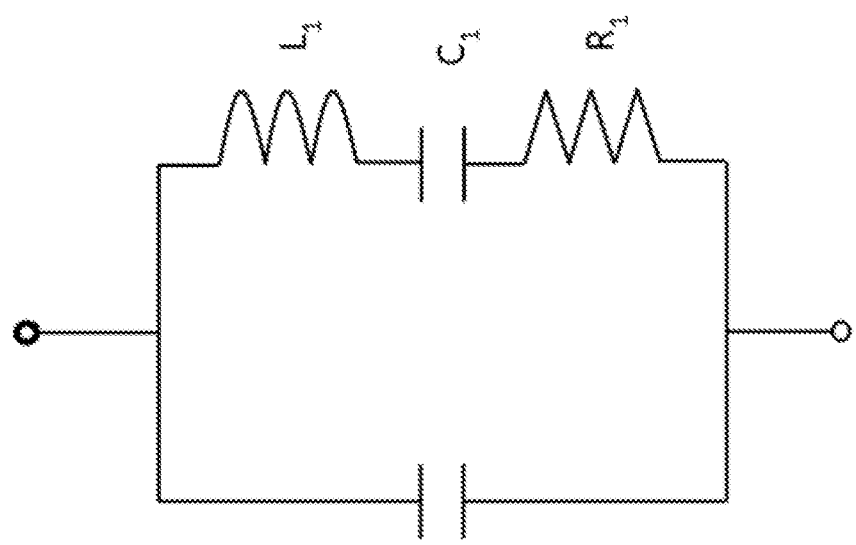
FIG. 27 is a schematic illustration of an electrical circuit equivalent to a piezoelectric transducer at mechanical resonance.
Figure 26:
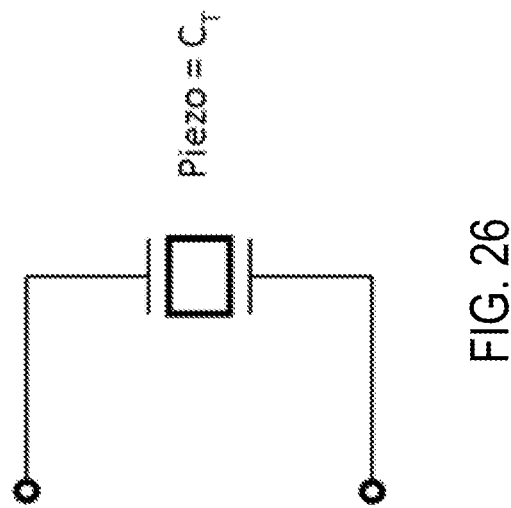
FIG. 26 is a schematic illustration of an electrical circuit equivalent to a piezoelectric transducer outside of mechanical resonance.

Apart from mechanical resonance, the piezo transducer 30 can be mostly capacitive in nature because piezoelectric elements in the transducer are arranged between electrodes and the piezoelectric elements serve as the dielectric, thereby forming a capacitor. At resonance, the piezoelectric transducer 30 can be modeled as an electrical equivalent circuit that behaves like a circuit composed of an inductor, capacitor, and resistor with a precise resonant frequency (FIG. 27). When the field is removed, the crystal will generate an electric field as it returns to its previous shape, and this can generate a voltage. The electrical circuit equivalent of the piezo transducer describes the change in mechanical properties, such as elastic deformation, effective mass (inertia), and mechanical losses resulting from internal friction. However, this description of the piezoelectric transducer can only be used for frequencies in the vicinity of the mechanical intrinsic resonance. By changing the dimensions and contours of the transducer masses, or by changing how the transducer is loaded, the operating frequency along with electrical and acoustic characteristics can be customized for specific applications.

Further amplification and mechanical efficiency of the transducer can be accomplished using known techniques, such as changing the internal faces of the masses that contact the piezoelectric elements to help propagate ultrasonic waves through the masses. Shallow cavities on the inner surfaces of the masses can create a mechanical transformer, whereby a portion of the radial motion of the ceramic driving elements is transferred and amplified by the metal plates in axial direction.

Referring again to at least FIGS. 1-3, the body 20 can support an internal (not shown) or external fluid source 92, shown as coupled to the body 20 via a port or connector 94 that can include threads, a luer attachment, a quick connect feature or any other suitable attachment feature. The transducer 30 can include a through channel 46 (FIG. 14B) extending through the horn first segment 34 and the horn second segment 40. FIG. 3 further illustrates the connection of the internal fluid line 90 from the connector 94 to or through the piezoelectric transducer 30. Fluid can flow from the fluid supply 92 (see FIG. 2) through the inside of the device 10 via the internal fluid line 90 and the horn through channel 46 and out though the dental tip 110. Other fluid configurations are described infra.

Figure 7A:
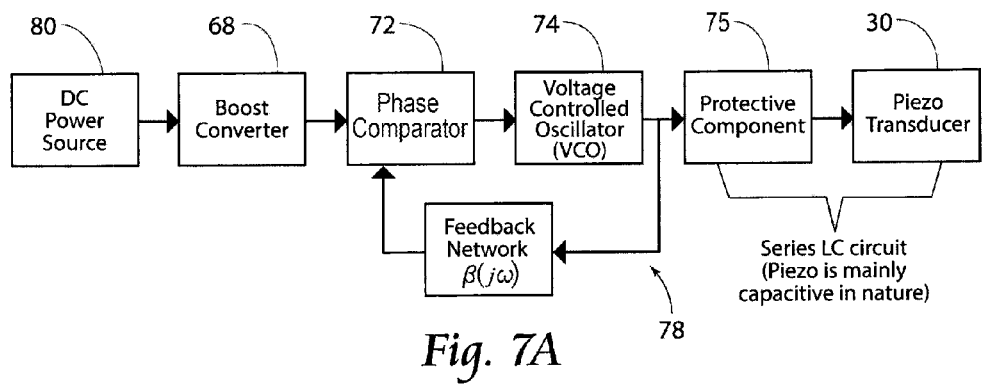
FIG. 7A is a first example schematic of the current flow through the circuitry of FIG. 6.
Figure 7B:
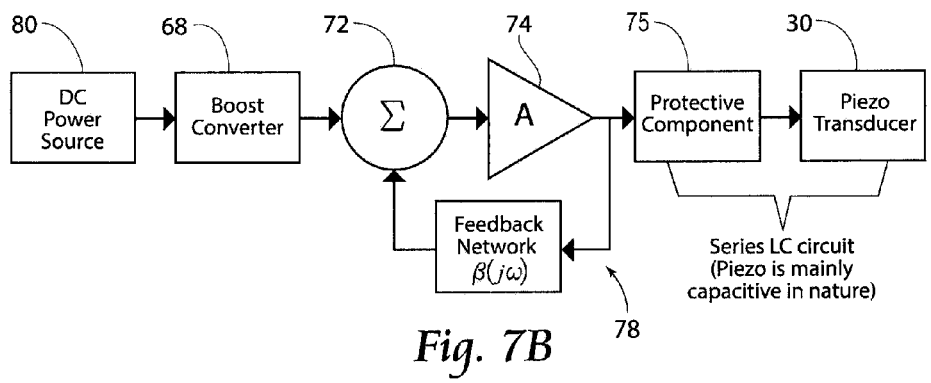
FIG. 7B is a second example schematic of the current flow through the circuitry of FIG. 6.

The aforementioned circuitry 70 confers particular advantages on devices in accord with the disclosure. The circuitry 70 generally includes a boost converter 68, a phase comparator 72, a low pass filter 76, a voltage controlled oscillator ("VCO") 74, and a feedback network 78. The electronic circuitry 70 can drive the transducer 30 at its mechanical resonance. FIGS. 7A and 7B show a flow diagram of a potential electrical path through the device 10. FIG. 7B incorporates schematic symbols for the phase comparator 72, a low pass filter 76 and the VCO 74. The circuitry 70 can also include the power supply 80, shown here as a DC power source. The power supply can include at least one battery. In one embodiment, the battery is a single cell lithium ion battery with an energy capacity of about 2 to about 10 Watt-hours and is capable of supplying an output current of between about 0.5 A and about 3 A during operation. Additionally, it is contemplated that the at least one battery can be rechargeable either by direct electrical contact charging, induction charging, or a combination thereof (see FIG. 19). Moreover, the circuitry 70 or 170 can include one or more protective components 75 such as one or more inductors, one or more diodes, or a combination thereof.

In some embodiments, the circuitry 70 includes an LC tank circuit or LC electrical resonator. In general, an LC tank circuit can have a frequency selective filter including an inductor (L) and capacitor (C) connected together. The LC tank circuit shown and described herein more efficiently drives the piezoelectric transducer. The circuit can be self adjusting to drive the transducer at its mechanical resonance. Charge flows back and forth between the capacitor's plates through the inductor, so the tuned circuit can store electrical energy oscillating at its resonant frequency. There are small losses in the "tank" (i.e., LC) circuit, but the amplifier feed by the signal from the VCO compensates for those losses and supplies the power for the output signal to compensate for the electrical and mechanical losses of the system. This combination and arrangement of circuit elements results in a low power consumption electronic circuit. By driving the transducer at or near resonance and by using the series inductor the circuit driving losses can be minimized. Further the system can have a high "Q". For example, one such circuit design is capable of generating a drive with a "Q" of about 5 to about 20. In this case Q=Gain (G)=about 5 to about 20. Therefore, about ⅕ to about 1/20 of the power is required for a piezoelectric scaler according to the present disclosure to produce the same work output of a design including hard switching.

It can be advantageous to select the circuit elements of the inductor and capacitor so that their resonance frequency is higher than that of the mechanical resonance of the piezoelectric transducer, but less than the $3^{rd}$ harmonic mechanical resonance of the piezoelectric transducer. FIG. 2 (below) is an example of a fundamental frequency sinusoidal waveform to the piezo transducer. If the $3^{rd}$ harmonic mechanical resonance (or higher order harmonics) is not appropriately filtered by the combination of Lser and Cpar, $3^{rd}$ harmonic oscillations can become dominant in the drive waveform and yield nonuseful and nonproductive mechanical output on the piezo transducer. For dental and medical piezoelectric devices, the resonance frequency of the added LC tank circuit can be in the range of about 60 kHz to about 120 kHz. Furthermore, the capacitance can be selected so that it is larger than the parallel capacitance of the piezoelectric transducer not at resonance. In one example, a 10 mm outer diameter×5 mm inner diameter×2 mm height piezoelectric ceramic disc element has a capacitance value around 300 pF. A piezoelectric transducer incorporating a stack of 4 piezoelectric crystals would have an approximate value of about 1.2 nF, so a suitable capacitance value would be about 4.7 nF. These parameters can restrict the allowable inductance value to between about 0.37 mH and about 1.5 mH, providing a resonance frequency in the above-specified ranges.

Figure 8:
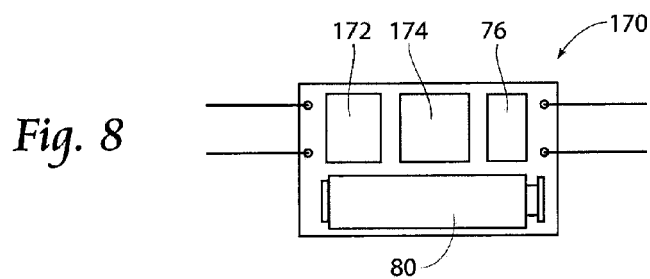
FIG. 8 is an illustration of another embodiment of the internal circuitry of a device according to the present disclosure.

FIG. 8 is an example illustration of an embodiment 170 of the circuitry of the device 10. Here, the circuitry 170 includes an inverter 172, and a frequency divider 174. Additional circuit elements can provide the ability to regulate both incoming and outgoing voltage.

Figure 9:
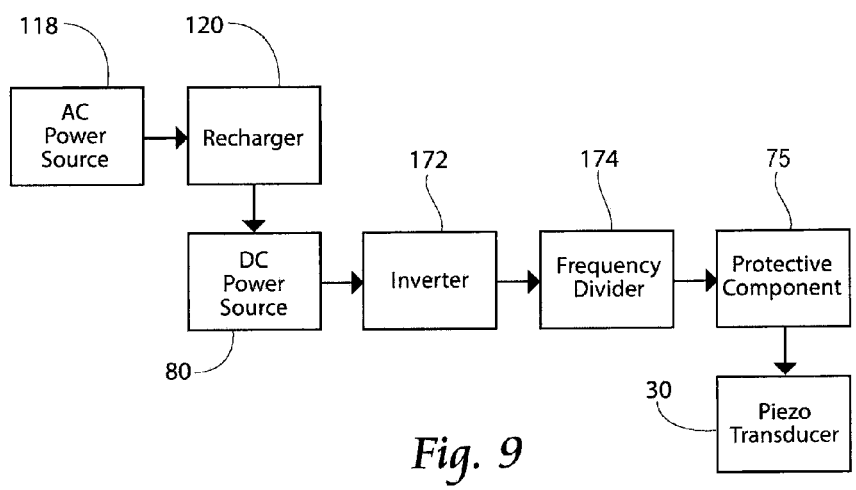
FIG. 9 is a schematic of the current flow through the dental device circuitry of FIG. 8.

FIG. 9 illustrates a general schematic illustrating one potential flow of current through the device 10 according to the embodiment incorporating the circuitry 170 illustrated in FIG. 8. Here, current flows from the power supply 80 to the inverter 172. Preferably, the applied voltage is delivered in a sine wave or impulse waveform in the Megahertz range. The inverter 172 thereby inverts the incoming direct current from the battery 80 to achieve this.

Supplying power at a frequency in the Megahertz range can be more efficient and enable the use of smaller electrical components as compared with the use of other frequencies. However, it can be useful to operate a device or circuit according to the present disclosure at an alternative or additional operational frequency. In one aspect, the current can be passed through the frequency divider 174 to alter the input signal and output a signal frequency that is a fraction of the input signal frequency. In one aspect, the output signal can be in the kilohertz range. In another aspect, the output signal can be selected to provide an operational frequency that is matched to the mechanical resonance of the transducer when loaded. Furthermore, it is contemplated that current can first flow from an alternating current source 118, through a transformer, rectifier, filter, and regulator (collectively 120) to recharge the at least one battery 80.

Additionally, it should be noted that alternative current paths capable of achieving the operation characteristics described herein are also contemplated. For instance, current can also flow to or from a switch, a control device, or a combination thereof positioned somewhere along the current path, the location of which can be based on optimization of the circuitry 70 and transducer 30 components.

Figure 20:
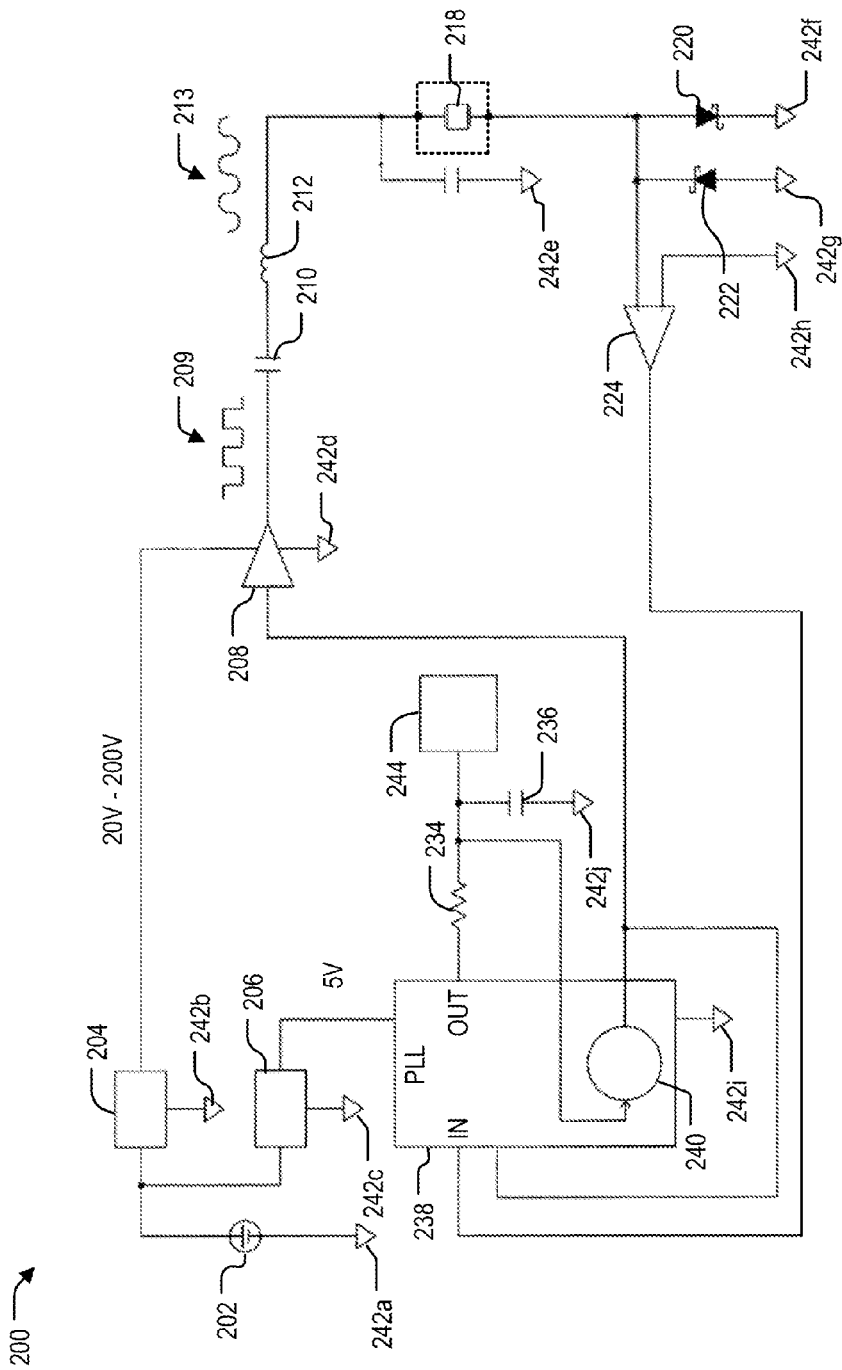
FIG. 20 is a schematic of an example configuration of a circuit according to the present disclosure.

FIG. 20 is a demonstrative illustration of an alternative configuration 200 of the circuitry 70 of the device 10. The circuitry of the device 10 in this alternative configuration 200 includes a battery 202 connected between a ground 242a and a first boost converter 204 and a second boost converter 206. The first boost converter 204 is connected to a first ground 242b and the second boost converter 206 is connected to a second ground 242. The output of the first boost converter 204 is between about 20 V to about 200 V and leads to a square wave driver 208. The output of the second boost converter 206 is about 5 V and provides power to a phase-locked loop (PLL) 238. The square wave driver 208, which generates a high voltage square wave output 209, is in series with a capacitor 210 and an inductor 212. The inductor 212 converts the square wave output 209 into a sine wave output 213.

The combination of the capacitor 210 and the inductor 212 is connected in series with a piezoelectric transducer 218. The capacitor 210 can remove the DC component from the piezoelectric transducer 218. The piezoelectric transducer 218 is connected in series with a first diode 220 and a second diode 222. The first diode 220 and a second diode 222 can be Schottky diodes. The first diode 220 and the second diode 222 are connected in parallel with each other and are connected to respective grounds 242f and 242g. The junction of the piezoelectric transducer 218, the first diode 220, and the second diode 222 is one input to a voltage comparator 224, with the other input to the voltage comparator 224 being a ground 242h.

The output of the voltage comparator 224, which can indicate the direction and phase of the current in the circuit 200, is an input to the phase comparator (in PLL 238). The output of the phase comparator goes to the low pass filter that includes resistor 234 and capacitor 236 which feeds into a voltage-controlled oscillator (VCO) 240. The PLL 238 includes the combination of the phase comparator, low pass filter, and VCO 240. The output of the voltage-controlled oscillator 240 is another input to phase comparator 238 and is also an input to the square wave driver 208. Block 244 includes a frequency limiting circuit. If a disturbance causes the system's frequency to exceed the resonant frequency of the crystal, the phase can get switched, and the PLL 238 can run into an upper rail. This can be detected by monitoring the voltage on the low pass filter. If the voltage approaches the upper rail, the voltage can be momentarily pulled back to ground (the lowest operating frequency) and released so the PLL 238 can once again acquire frequency lock on the crystal. Other possible limiters such as a comparator with appropriate feedback networks can also be used.

The phase lock loop synchronizes the drive voltage to the phase of the current through the ceramic. The PLL 238 detects where the impedance is the lowest or where the phase crosses zero (i.e. where the reactive elements—capacitor and inductor—become electrically a short circuit and the phase between the input and output waveforms is a zero phase shift).

The piezoelectric transducer 218 operates at a higher unloaded resonance frequency, but when loaded by a surgical or treatment tip, operates within the range of about 25 kHz to about 50 kHz. The surgical or treatment tip can be any tip designed for the transmission of ultrasonic energy when coupled to a piezoelectric device. For example, a suitable treatment tip can include any tip for use with current dental scaler devices. In one aspect, a treatment tip can be a flexible, bendable, or rigid ultrasonic tip to allow for a user to define the contra-angle and still provide adequate energy transfer. Circuitry according to the present disclosure can omit a smoothing circuit, as the combination of the capacitor 210 and the inductor 212 can create the sinusoidal drive output signal 213. It can be useful to provide a sinusoidal drive to reduce the rate of wear on a treatment tip, improve patient comfort, or a combination thereof.

Figure 14A:
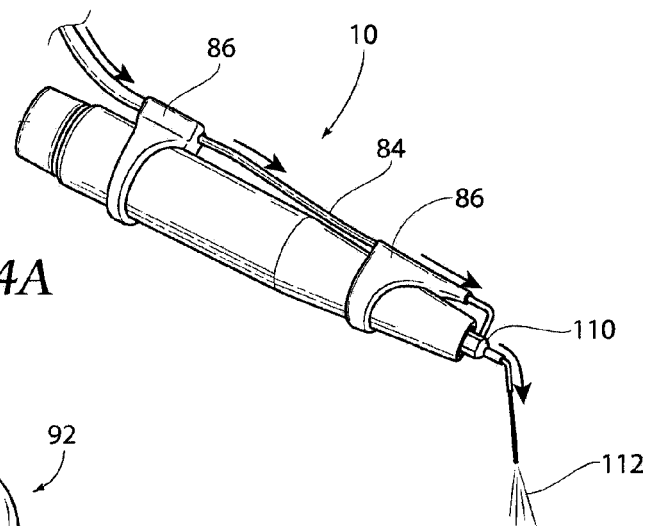
FIG. 14A is a perspective view of a device according to the present disclosure illustrating the flow of fluid along an external fluid path.

FIGS. 10-12 illustrate additional fluid delivery embodiments. FIG. 10 shows a remote fluid source 82 and an external fluid line 84. The external fluid line 84 can be removably secured to the device 10 by way of clips 86 or other suitable attachment methods. Turning to FIG. 14A, fluid 112 flows from the remote fluid source 82, through the external fluid line 84, to the procedure site either through the interior of the dental tip 110 as shown here or along the exterior of the dental tip 110. Additional or alternative methods of fluid delivery are also contemplated. For example, the fluid can initially travel through an external bore of a treatment tip before flowing towards to the exterior of the treatment tip in order to flow along an exterior surface thereof.

FIG. 11 illustrates a collinear fluid supply 88, which can be an elastomeric pump, removably attached to the end of the device opposite the dental tip 110. A fluid inlet (not shown) can be located opposite the location of attachment to the device 10 to allow filling of the collinear fluid supply 88 while attached to the device 10. Fluid 112 can flow external to the device 10 (see FIG. 14A) or can flow through the device 10 by way of an internal fluid line 90 and the through channel 46 (see FIG. 14B) and out through the dental tip 110. Additionally, the power switch 130 is shown positioned on the body 20 of the device 10 in this embodiment.

FIG. 12 shows a radially mounted fluid source 92 that can include a fillable non-powered fluid source 100. As a non-limiting example, the non-powered fluid source shown here is an elastomeric pump. However, any device capable of using potential energy to expel liquid from its interior by the nature of the container material's elasticity is contemplated.

The elastomeric pump 100 includes an input 102, an elastomeric bladder 104, and an output 106 (see FIG. 13). The input 102 can be configured to receive a syringe 122 (see FIG. 15) and can include a one-way valve. The output 106 can also include a one-way valve and can be removably attached and operatively connected to the internal fluid line 90 through a connector 94 located on the periphery of the device 10.

The non-powered fluid source 100 promotes a constant flow rate of the fluid 112 by expending potential energy stored in a filled elastomeric bladder 104. The fluid 112 can be delivered to and through the device 10 without the need of electricity and separate from the power source and the piezoelectric stack thereby reducing the overall electricity demand of the device 10.

Figure 14B:
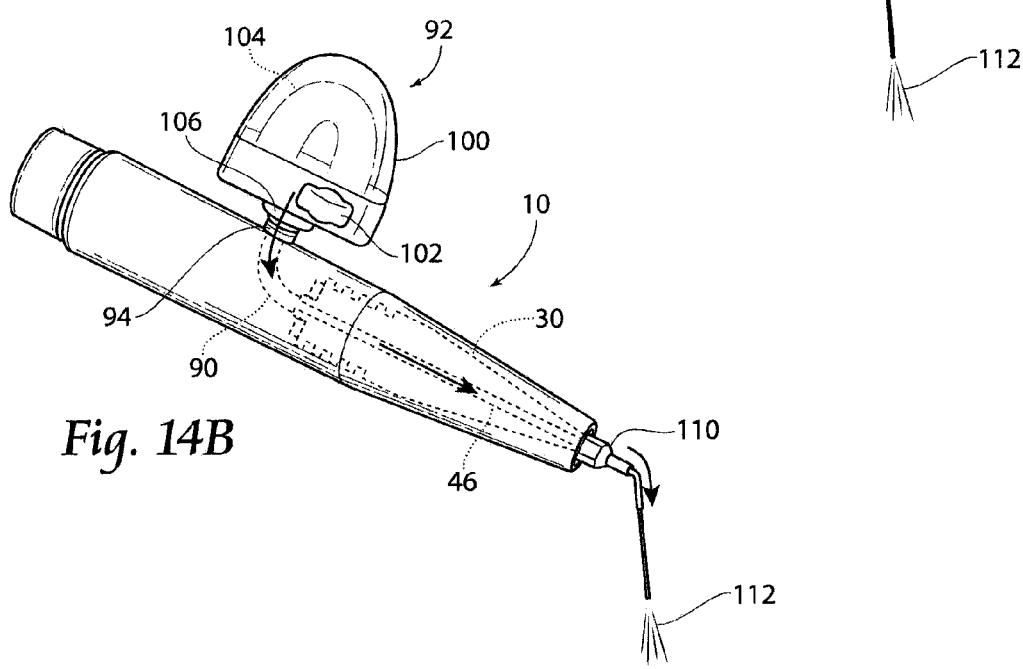
FIG. 14B is a perspective view of a dental device according to the present disclosure illustrating the flow of fluid along an internal fluid path.

FIG. 14B illustrates the flow path of the fluid from the radially mounted fluid source 92 through the device 10. The fluid can include any number of dental solutions including water, saline, bleach, CHX, EDTA, Listerine, Peridex, and other solutions commonly used in prophylaxis and other dental procedures. First, the fluid 112 exits the output 106 of the elastomeric infusion pump 100 and travels through the internal fluid line 90. The internal fluid line 90 can operatively connect with or extend through the transducer through channel 46. The fluid 112 then flows through the connected dental tip 110 and out to the procedure site.

Figure 15:
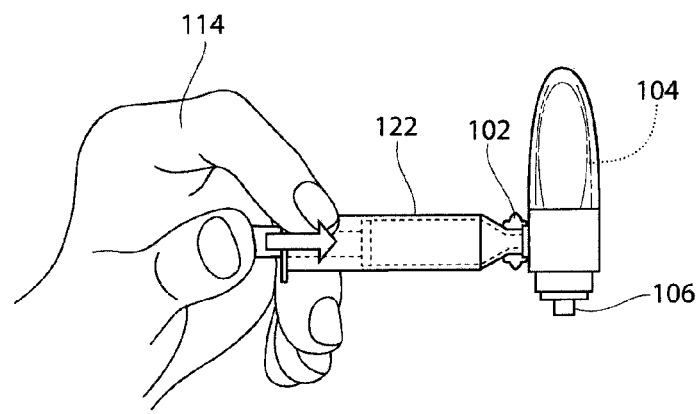
FIG. 15 is a side view of the fluid supply of FIG. 11 attached to a syringe.

FIGS. 15-18 show the operation of the device 10. In FIG. 15 the fluid source 100 is filled by a syringe 122. The interface between the syringe 122 and the fluid source 100 can be accomplished by way of a luer lock fitting or any way known in the art.

Figure 16:
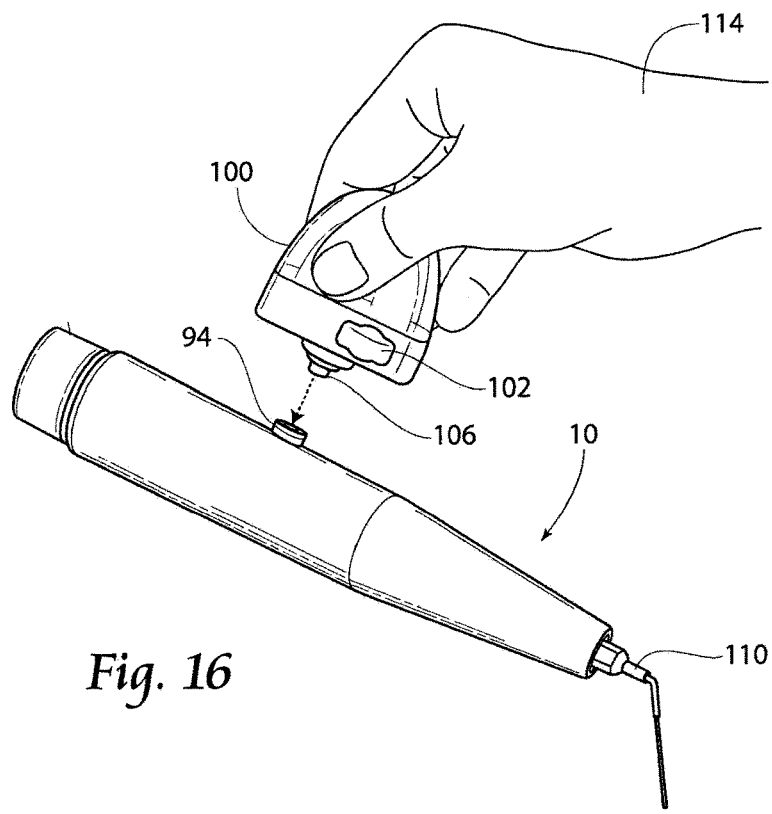
FIG. 16 is a perspective view of the device of FIG. 12 showing the fluid supply of FIG. 13 positioned apart from the device for attachment thereto.

FIG. 16 illustrates the attachment of the elastomeric infusion pump 100 to the device 10. A luer lock fitting or comparable fitting can be used in this interface as well.

Figure 17:
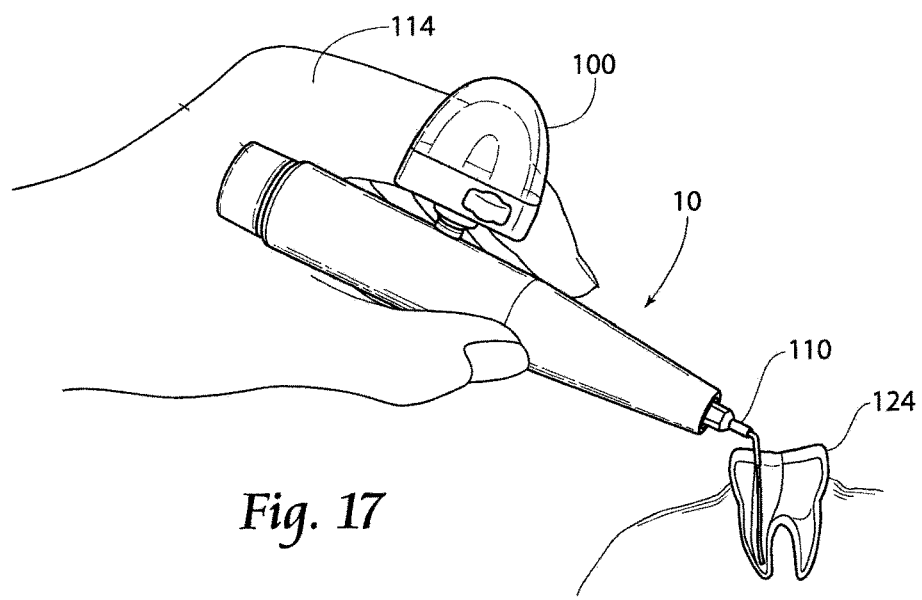
FIG. 17 is a perspective view of the device of FIG. 12 in use.
Figure 18:
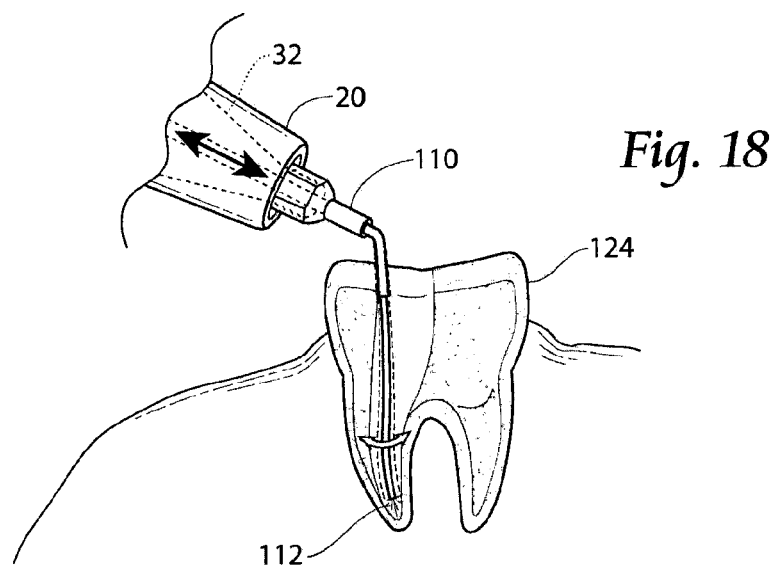
FIG. 18 is an enhanced view of FIG. 17 showing the device in use.

As shown in FIG. 17, the device 10 is shown in an operator's hand 114 with the dental tip 110 located at or near the procedure site. FIG. 18 further illustrates the mechanical operation of the transducer 30 and the dental tip 110. The preferred voltage applied to piezoelectric stack 50 is about 100 V to about 800 V peak-to-peak. The vibrations created by the linear movement of the piezoelectric stack 50 are carried through the horn 32 and out to the dental tip 110 resulting in an oscillatory movement. The fluid 112 enters the procedure site, for example, through the dental tip 110.

Figure 19:
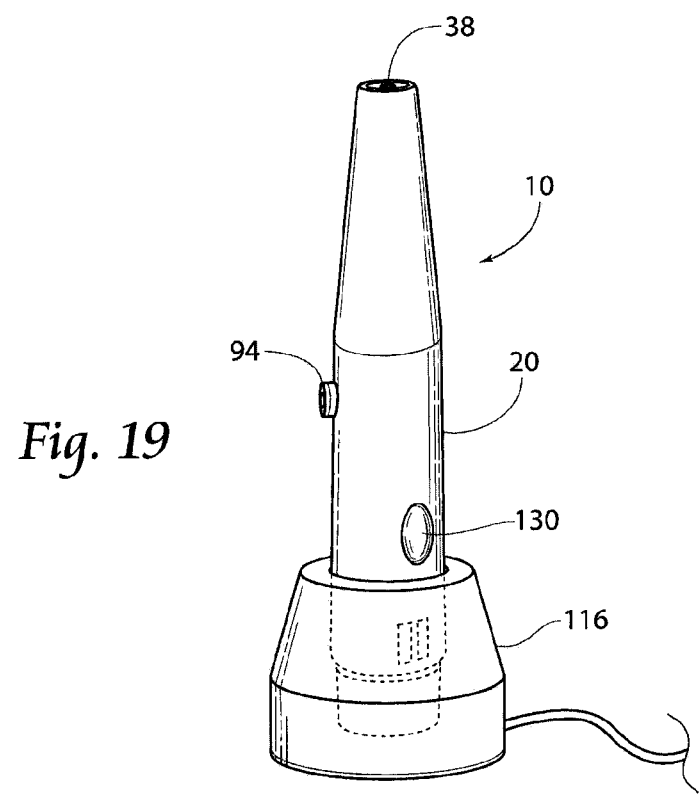
FIG. 19 is a perspective view of the device of FIG. 12 in a charging station.

FIG. 19 exemplifies a charging station 116 that can be plugged into any standard A/C outlet (e.g., 120V or 240V) to recharge the power supply 80. The power supply can alternatively be recharged by direct electrical contact charging or by induction charging.

Another configuration of the device 10 is shown in FIGS. 21-24. FIG. 21 illustrates a perspective view of a device 300. The device 300 has a body 302 having a distal end 304 and a proximal end 306, an activation button 308, and a surgical or treatment tip 310.

As shown in FIG. 22, the device body 302 supports the circuitry 312 and the rechargeable energy source 313 at the proximal end 306 of the device 300. The circuitry 312 can be similar or identical to the circuitry 200 shown in FIG. 20. The rechargeable energy source can be a DC battery, a supercapacitor, a rechargeable battery, a lithium ion battery, the like, or combinations thereof. In one aspect, the rechargeable energy source can be combined with or omitted in place of any other energy source known in the art. In one embodiment, the rechargeable energy source can be omitted from the device, for example, in the case of a wired device that is electrically connected to an external energy source such as an external battery or a building outlet. In some embodiments, the body 302 can support a piezoelectric transducer 314 at the distal end 304 of the device 300. The piezoelectric transducer 314 can be similar or identical to the piezoelectric transducer 30 shown in FIG. 5.

FIG. 23 shows body 302 that includes a plurality of sections, for example the five sections 302A, 302B, 302C, 302D, and 302E that can snap together using clips 316 or joined with screws. The sections are configured to house the circuitry 312, the battery 313, and the piezoelectric transducer 314 so that the circuitry 312 and the battery 313 are tightly in place and the piezoelectric transducer 314 has freedom to move as needed.

Figure 24:
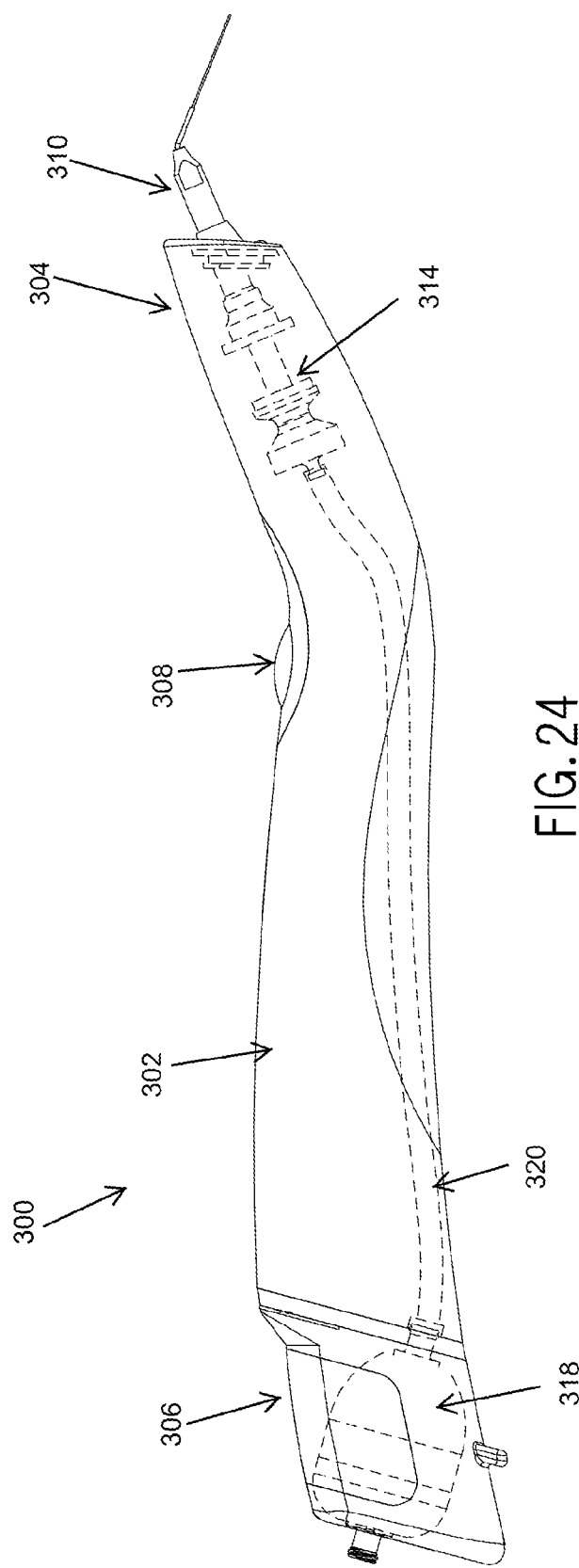
FIG. 24 is a side view of the device illustrated in FIG. 21 showing a fluid pump incorporated therein as indicated by dashed lines.

Turning to FIG. 24, the fluid pump 318 can be, e.g., an elastomeric infusion pump or a piezoelectric pump of the type available from Dolomite Microfluidics, CurieJet, Schwarzer Precision, Takasago Fluidic Systems, and Bartels Mikrotechnik. However, other piezoelectric pumps that meet the power, size and flow rate requirements of the device are contemplated. In one embodiment, a piezoelectric pump can provide fluid delivery and irrigant flow rates of about 0.01 mL to about 20 mL per minute and consume power less than about 500 mW during operation. In another embodiment, a piezoelectric pump can provide fluid delivery and irrigant flow rates of about 2 mL to about 10 mL per minute. The fluid pump 318 can be configured to pump a fluid, such as water, through the device 300 by way of fluid line 320. The fluid can flow through fluid line 320 and the piezoelectric transducer 314 and the tip 310. In other configurations, the fluid pump 318 is not incorporated into the device 300 and can either be attachable to the device 300 or partially or completely external and connected to the device via a separate fluid line. Regardless of the fluid path, the device 300 can incorporate materials that are compatible with the aforementioned irrigants and can require further processing of the metallic parts to ensure reliability of the device 300.

The device 300 can be controlled by a wired or wireless foot pedal, a central control unit that operates wirelessly to the handheld device, or by another similar means so as to control the 'on' and 'off' operations of the device 300, power setting (in other words, applied voltage to piezoelectric ceramic), and fluid delivery flow rates commonly observed in tethered bench top units.

EXAMPLES

Figure 25:
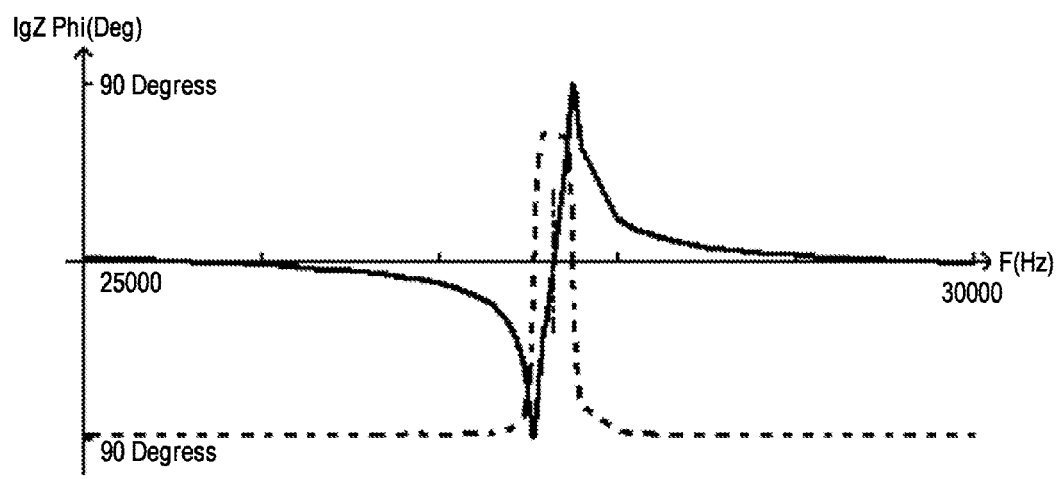
FIG. 25 is a plot of impedance as a function of phase angle for a commercially available piezoelectric transducer connected to a dental hygiene treatment tip.

With reference to FIG. 25, an example device according to the present disclosure having a circuit as shown in FIG. 20 was loaded with a treatment tip. The treatment tip was an ultrasonic dental hygiene scaling tip designed for removal of dental plaque and calculus build up, and was securably coupled to the ultrasonic dental transducer headpiece with a torque wrench. The leads to the ultrasonic handpiece were then connected to an impedance analyzer to obtain electrically equivalent circuit parameters and features related to the mechanical resonance of the coupled handpiece and treatment tip system. Impedance and phase spectra were collected by a Bandera PV70A impedance analyzer designed for collecting data from high power ultrasonic transducers. The resonant frequency ($F_s$) was determined to be 27,536 Hz by identifying where the impedance is a local minimum and the phase is zero. Further parameters related to the present example are shown in Table 1 below. Based on the measured values for $C_T$ and $F_S$, suitable parameters for the parallel capacitor and series inductor are as follows: Cpar=4.7 nF and Lser would be between about 1.0 mH and about 5.25 mH to ensure that the combined Lser+Cpar resonance frequency is larger than the mechanical resonance of the transducer, but less than the 3$^{rd}$ harmonic mechanical resonance (i.e. 27,536 Hz and 82,608 Hz, respectively).

TABLE 1

| Parameter | Units | Value |
|---|---|---|
| $F_s$ | Hz | 27536.0 |
| $F_1$ | Hz | 27518.2 |
| $F_2$ | Hz | 27553.6 |
| $Q_m$ | — | 777.8 |
| $G_{max}$ | Ms | 2.67 |
| $R_1$ | Ohm | 374.7 |
| $F_p$ | Hz | 27750 |
| $K_{eff}$ | — | 0.124 |
| $C_T$ | nF | 1.350 |
| $C_0$ | nF | 1.330 |
| $C_1$ | nF | 0.020 |
| $L_1$ | mH | 1684.6 |
| $Z_{max}$ | kOhm | 48.7 |
| $F_0$ | — | 27643 |

The terminology used herein is for the purpose of describing particular embodiments only and is not intended to be limiting of the disclosure. As used herein, the singular forms "a", an and the are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Explicitly referenced embodiments herein were chosen and described in order to best explain the principles of the disclosure and their practical application, and to enable others of ordinary skill in the art to understand the disclosure and recognize many alternatives, modifications, and variations on the described example(s). Accordingly, various embodiments and implementations other than those explicitly described are within the scope of the following claims.

What is claimed is:

1. A device, comprising:
   a circuit, comprising:
   at least one boost converter configured to receive power from an energy source;
   a square wave driver configured to receive power from the boost converter and to generate a high voltage square wave;
   a distally mounted piezoelectric transducer driven by the square wave driver, and connectable to a load;
   first and second grounded diodes arranged back-to-back and configured in parallel with each other, the diodes connected in series with the transducer and arranged to form a junction between the transducer and ground; and
   a voltage comparator having a first input connected to the junction, and an output that indicates phase of current through the transducer as a voltage; and
   coupled to the circuit, a phase-locked loop in a feedback loop, the phase-locked loop comprising a low pass filter, a voltage-controlled oscillator (VCO), and a phase comparator having a first input for receiving from the VCO a voltage that indicates a drive voltage phase and having a second input for receiving the voltage comparator output voltage,
   whereby when the transducer is connected to the load the phase-locked loop synchronizes the current phase and the drive voltage phase to determine a resonance frequency of the transducer.

2. The device of claim 1, wherein the energy source is a direct current rechargeable battery, and wherein the energy source is integral to the circuit.

3. The device of claim 2, wherein the circuit further comprises a second boost converter powered from the direct current battery, and optionally wherein the output of the second boost converter provides power to the phase-locked loop.

4. The device of claim 1, wherein the circuit further comprises a capacitor in parallel with the transducer to suppress at least a 3rd harmonic mode of vibration of the transducer.

5. The device of claim 1, wherein the phase-locked loop is configured to synchronize drive voltage to the resonance frequency of the transducer when the transducer is connected to the load; and
   wherein said device comprises a frequency limiting circuit coupled to the phase-locked loop.

6. The device of claim 1, further comprising a fluid pump, optionally wherein the fluid pump is selected from the group consisting of an elastomeric infusion pump and a piezoelectric pump, and optionally wherein said pump is capable of producing flow rates between 0.01 ml-20 ml per minute to a treatment site.

7. The device of claim 1, wherein the load is a treatment tip for a procedure selected from the group consisting of a dental procedure and a medical procedure.

8. The device of claim 1, wherein the transducer is of 40-60 mm in length and has:
   a loaded resonance frequency of between 25-50 kHz,
   a backmass characterized by rings of varying radii,
   a stack comprising between 2 and 8 piezoelectric discs electrically connected in parallel and mechanically connected in series, and
   a tapered horn;
   wherein said circuit is capable of producing an applied voltage waveform of between 100 and 800 volts peak-to-peak.

9. The device of claim 1, further comprising an inductor in series with the square wave driver.

10. The device of claim 9, wherein the circuit further comprises a capacitor in series with the inductor.

11. A cordless handheld ultrasonic device comprising:
    a device body having a distal end for coupling to at least one treatment tip; and
    a circuit within the device body, the circuit comprising:
    at least one boost converter configured to receive power from an energy source;
    a square wave driver configured to receive power from the boost converter and to generate a high voltage square wave;
    a distally mounted piezoelectric transducer driven by the square wave driver;
    first and second grounded diodes arranged back-to-back and configured in parallel with each other, the diodes connected in series with the transducer and arranged to form a junction between the transducer and ground, a voltage comparator having a first input connected to the junction, and an output that indicates phase of current through the transducer as a voltage; and coupled to the circuit, a phase-locked loop in a feedback loop, the phase-locked loop comprising a low pass filter, a voltage controlled oscillator, and a phase comparator having a first input for receiving from the voltage-controlled oscillator a voltage that indicates a drive voltage phase and having a second input for receiving the voltage comparator output voltage to determine a resonance frequency of the piezoelectric transducer when the piezoelectric transducer is connected to the at least one treatment tip.

12. The cordless handheld ultrasonic device of claim 11, wherein the circuit further comprises an energy source, the at least one boost converter in series with the energy source and wherein the circuitry further comprises a second boost converter in series with the energy source.

13. The cordless handheld ultrasonic device of claim 12, wherein the output of the second boost converter is an input to the phase-locked loop.

14. The cordless handheld ultrasonic device of claim 12, wherein the energy source is a rechargeable battery.

15. The cordless handheld ultrasonic device of claim 11, wherein the piezoelectric transducer is connectable to a treatment tip for a procedure selected from the group consisting of a dental procedure and a medical procedure.

16. The cordless handheld ultrasonic device of claim 11, wherein the phase-locked loop is configured to synchronize drive voltage to the resonance frequency of the transducer when the transducer is connected to the load; and wherein said device comprises a frequency limiting circuit coupled to the phase-locked loop.

17. The cordless handheld ultrasonic device of claim 11, further comprising a fluid pump, optionally wherein the fluid pump is selected from the group consisting of an elastomeric infusion pump and a piezoelectric pump, and optionally wherein said pump is capable of producing flow rates between 0.01 ml-20 ml per minute to a treatment site.

18. The device of claim 11, wherein the transducer is of 40-60 mm in length and has:
a loaded resonance frequency of between 25-50 kHz,
a backmass characterized by rings of varying radii,
a stack comprising between 2 and 8 piezoelectric discs electrically connected in parallel and mechanically connected in series, and
a tapered horn;
wherein said circuit is capable of producing an applied voltage waveform of between 100 and 800 volts peak-to-peak.

19. The device of claim 11, further comprising an inductor in series with the square wave driver.

20. The cordless handheld ultrasonic device of claim 19, further comprising a capacitor in series with the inductor.

21. A device, comprising:
a circuit, comprising:
at least one boost converter configured to receive power from an energy source;
a square wave driver configured to receive power from the boost converter and to generate a high voltage square wave;
a distally mounted piezoelectric transducer driven by the square wave driver and, connectable to a load;
first and second grounded diodes arranged back-to-back and configured in parallel with each other, the diodes connected in series with the transducer and arranged to form a junction between the transducer and ground; and
a voltage comparator having a first input connected to the junction, and an output that indicates phase of current through the transducer as a voltage; and
a feedback loop coupled to the circuit to determine a resonance frequency of the piezoelectric transducer when the piezoelectric transducer is connected to the load.

22. The device of claim 21, wherein the energy source is a direct current rechargeable battery, and wherein the energy source is integral to the circuit.

23. The device of claim 22, wherein the circuit further comprises a second boost converter powered from the direct current battery, and optionally wherein the output of the second boost converter provides power to the feedback loop.

24. The device of claim 21, wherein the circuit further comprises a capacitor in parallel with the piezoelectric transducer to suppress at least a 3rd harmonic mode of vibration of the piezoelectric transducer.

25. The device of claim 21, wherein the feedback loop is configured to synchronize drive voltage to the resonance frequency of the transducer when the transducer is connected to the load; and wherein said device comprises a frequency limiting circuit coupled to the feedback loop.

26. The device of claim 21, further comprising a fluid pump, optionally wherein the fluid pump is selected from the group consisting of an elastomeric infusion pump and a piezoelectric pump, and optionally wherein said pump is capable of producing flow rates between 0.01 ml-20 ml per minute to a treatment site.

27. The device of claim 21, wherein the load is a treatment tip for a procedure selected from the group consisting of a dental procedure and a medical procedure.

28. The device of claim 21, wherein the transducer is of 40-60 mm in length and has:
a loaded resonance frequency of between 25-50 kHz,
a backmass characterized by rings of varying radii,
a stack comprising between 2 and 8 piezoelectric discs electrically connected in parallel and mechanically connected in series, and
a tapered horn;
wherein said circuit is capable of producing an applied voltage waveform of between 100 and 800 volts peak-to-peak.

29. The device of claim 21, further comprising an inductor in series with the square wave driver.

30. The device of claim 29, wherein the circuit further comprises a capacitor in series with the inductor.

* * * * *